(12) United States Patent
Teller et al.

(10) Patent No.: US 10,925,376 B2
(45) Date of Patent: Feb. 23, 2021

(54) LIP BALM WITH SPHERICAL SURFACE AND METHOD FOR PRODUCING

(71) Applicant: EOS PRODUCTS, LLC, New York, NY (US)

(72) Inventors: Jonathan Teller, New York, NY (US); Craig Dubitsky, Montclair, NJ (US); Coral Garvey, Brooklyn, NY (US); Dennis Payongayong, Brooklyn, NY (US)

(73) Assignee: EOS PRODUCTS, LLC, New York, NY (US)

( * ) Notice: Subject to any disclaimer, the term of this patent is extended or adjusted under 35 U.S.C. 154(b) by 0 days.

(21) Appl. No.: 16/371,437

(22) Filed: Apr. 1, 2019

(65) Prior Publication Data

US 2019/0269220 A1    Sep. 5, 2019

Related U.S. Application Data

(63) Continuation of application No. 15/441,886, filed on Feb. 24, 2017, now Pat. No. 10,278,477, which is a (Continued)

(51) Int. Cl.
*A45D 40/20* (2006.01)
*A45D 40/00* (2006.01)
(Continued)

(52) U.S. Cl.
CPC ......... *A45D 40/0068* (2013.01); *A45D 40/00* (2013.01); *A45D 40/12* (2013.01); (Continued)

(58) Field of Classification Search
CPC .. A61Q 19/001; A45D 40/0068; A45D 40/12; A45D 40/26; A45D 40/16; A45D 2040/0012
See application file for complete search history.

(56) References Cited

U.S. PATENT DOCUMENTS

| 75,524 A | 2/1868 | Chase |
| 225,785 A | 3/1880 | Beattie |

(Continued)

FOREIGN PATENT DOCUMENTS

| EP | 0 433 150 | 6/1991 |
| EP | 0 628 393 | 4/1994 |

(Continued)

OTHER PUBLICATIONS

U.S. Appl. No. 29/411,931, filed Jan. 2012, Teller.
(Continued)

*Primary Examiner* — Jennifer C Chiang

(57) ABSTRACT

A lip balm applicator product comprises upper and lower portions that are connectable together to define the applicator product being of a substantially spherical shape. A support platform is located in the lower portion and accommodates a quantity of lip balm having an arcuate surface. A lip balm comprises a composition of waxes and oils in solid form and formed to have an arcuate surface. The composition is formed to have the arcuate surface using a hot pour process. A method of manufacturing a lip balm comprises providing a receptacle having a concave arcuate surface. A lip balm material in a heated, liquefied phase is poured into the receptacle. Once poured, the heated, liquefied phase is allowed to solidify such that a surface of the solidified lip balm material has an arcuate configuration that corresponds to the concave arcuate surface of the receptacle.

28 Claims, 4 Drawing Sheets

Related U.S. Application Data continuation of application No. 15/016,257, filed on Feb. 4, 2016, now Pat. No. 9,585,458, which is a continuation of application No. 13/941,204, filed on Jul. 12, 2013, now abandoned, which is a continuation of application No. 13/891,268, filed on May 10, 2013, now abandoned, which is a continuation of application No. 12/632,114, filed on Dec. 7, 2009, now Pat. No. 8,444,337.

(51) Int. Cl.

| | | |
|---|---|---|
| *A45D 40/16* | (2006.01) | |
| *A61K 8/31* | (2006.01) | |
| *A61K 8/92* | (2006.01) | |
| *A61Q 19/00* | (2006.01) | |
| *A61K 8/9789* | (2017.01) | |
| *A61K 8/9794* | (2017.01) | |
| *A45D 40/26* | (2006.01) | |
| *B29C 39/02* | (2006.01) | |
| *B65B 5/10* | (2006.01) | |
| *A45D 40/12* | (2006.01) | |

(52) U.S. Cl.
CPC ............. *A45D 40/16* (2013.01); *A45D 40/26* (2013.01); *A61K 8/31* (2013.01); *A61K 8/922* (2013.01); *A61K 8/925* (2013.01); *A61K 8/927* (2013.01); *A61K 8/9789* (2017.08); *A61K 8/9794* (2017.08); *A61Q 19/001* (2013.01); *B29C 39/026* (2013.01); *B65B 5/103* (2013.01); *A45D 2040/0012* (2013.01); *A61K 2800/87* (2013.01)

(56) References Cited

U.S. PATENT DOCUMENTS

| | | | |
|---|---|---|---|
| 1,852,455 A | 4/1932 | Friedman | |
| D112,545 S | 12/1938 | Younghusband | |
| 2,171,112 A | 8/1939 | Hoffman | |
| 2,201,467 A | 5/1940 | Bloom | |
| D129,291 S | 9/1941 | Petzold | |
| D130,030 S | 10/1941 | Meyer | |
| 2,314,338 A | 3/1943 | Graves et al. | |
| D158,174 S | 4/1950 | Busiel | |
| 2,568,688 A | 9/1951 | Sidney | |
| 2,745,642 A | 5/1956 | Herman | |
| D180,109 S | 4/1957 | Slater | |
| 2,859,085 A | 11/1958 | Morrison | |
| D189,888 S | 3/1961 | Tapper | |
| 2,998,896 A | 9/1961 | Miller | |
| 3,085,709 A | 4/1963 | Klein | |
| D200,724 S | 3/1965 | Grogel | |
| 3,292,840 A | 12/1966 | Schmidt | |
| 3,494,515 A | 2/1970 | Fattori | |
| D219,496 S | 12/1970 | Lebedeff | |
| 3,741,379 A | 6/1973 | Kappler et al. | |
| D228,157 S | 8/1973 | Sussman | |
| D230,954 S | 3/1974 | Gregorietti | |
| 3,843,120 A | 10/1974 | Ricci | |
| D240,711 S | 7/1976 | Angleman et al. | |
| D243,585 S | 3/1977 | Angleman et al. | |
| 4,044,889 A | 8/1977 | Orentreich et al. | |
| 4,124,135 A | 11/1978 | Weder et al. | |
| 4,164,301 A | 8/1979 | Thayer | |
| D253,394 S | 11/1979 | Berghahn et al. | |
| D255,653 S | 7/1980 | Lipsz | |
| D255,990 S | 7/1980 | Lucas | |
| D256,095 S | 7/1980 | Sandonato | |
| 4,235,557 A | 11/1980 | Hayes | |
| D258,199 S | 2/1981 | Torongo, Jr. | |
| 4,261,468 A | 4/1981 | Krebs | |
| D261,105 S | 10/1981 | Schwartz | |
| 4,342,522 A | 8/1982 | Mackles | |
| D266,146 S | 9/1982 | Morris | |
| 4,369,158 A | 1/1983 | Woodruff et al. | |
| D272,723 S | 2/1984 | Baker | |
| D273,766 S | 5/1984 | Lampe | |
| D280,289 S | 8/1985 | Aldrich, III et al. | |
| D286,616 S | 11/1986 | Becker | |
| 4,728,210 A | 3/1988 | Barish et al. | |
| 4,765,501 A | 8/1988 | Kao | |
| 4,781,483 A | 11/1988 | Lorscheidt | |
| D302,384 S | 7/1989 | Holewinski | |
| D317,118 S | 5/1991 | Crawford | |
| 5,025,817 A | 6/1991 | Wen | |
| 5,044,496 A | 9/1991 | Tanaka et al. | |
| 5,061,102 A | 10/1991 | Rennie | |
| D321,319 S | 11/1991 | Giuseppe | |
| 5,092,700 A | 3/1992 | Susini et al. | |
| 5,137,185 A | 8/1992 | Mitchell | |
| 5,167,462 A | 12/1992 | Lucas | |
| D333,780 S | 3/1993 | Jones et al. | |
| D333,784 S | 3/1993 | Goodman | |
| D337,757 S | 7/1993 | Wu | |
| D339,986 S | 10/1993 | Garouste et al. | |
| D343,699 S | 1/1994 | Yang | |
| 5,287,979 A | 2/1994 | Bourgeois | |
| D346,112 S | 4/1994 | Alcindor | |
| D354,441 S | 1/1995 | Fontanella | |
| D357,584 S | 4/1995 | Swingier | |
| D368,220 S | 3/1996 | Bicknell et al. | |
| 5,496,122 A | 3/1996 | Fattori | |
| D368,427 S | 4/1996 | Bicknell et al. | |
| 5,503,825 A | 4/1996 | Lane | |
| 5,542,557 A | 8/1996 | Koyama et al. | |
| D377,757 S | 2/1997 | Bertolini | |
| D387,662 S | 12/1997 | Bright | |
| D389,409 S | 1/1998 | Tucker | |
| 5,733,617 A | 3/1998 | Baduel | |
| D393,421 S | 4/1998 | Kovens | |
| 5,738,123 A | 4/1998 | Szekely | |
| 5,743,404 A | 4/1998 | Melashenko et al. | |
| 5,792,496 A | 8/1998 | Fekete et al. | |
| D398,533 S | 9/1998 | Kotyuk, Jr. et al. | |
| 5,799,667 A | 9/1998 | Szekely | |
| 5,808,215 A | 9/1998 | Kralik et al. | |
| 5,813,784 A | 9/1998 | Durliat | |
| D406,764 S | 3/1999 | Bright et al. | |
| 5,884,637 A | 3/1999 | Joulia | |
| D408,738 S | 4/1999 | Wu | |
| 5,897,263 A | 4/1999 | Fattori | |
| 5,925,391 A | 7/1999 | Whetstone, Jr. | |
| 5,988,424 A | 11/1999 | Kovens | |
| 6,010,264 A | 1/2000 | Scuderi et al. | |
| 6,029,842 A | 2/2000 | Sheffler et al. | |
| D422,904 S | 4/2000 | Lepsius et al. | |
| 6,050,438 A | 4/2000 | Kovens et al. | |
| 6,099,872 A | 8/2000 | Whetstone, Jr. | |
| 6,193,427 B1 | 2/2001 | Benguigui | |
| D443,726 S | 6/2001 | Faillant-Oumas | |
| 6,283,658 B1 | 9/2001 | Estevez et al. | |
| 6,391,972 B1 | 5/2002 | Hatakeyama | |
| D458,835 S | 6/2002 | Oelli-Venneri | |
| D459,216 S | 6/2002 | Heijdenrijk | |
| D465,614 S | 11/2002 | Petit | |
| D465,733 S | 11/2002 | Hill | |
| D466,252 S | 11/2002 | Yu | |
| D471,667 S | 3/2003 | Angeletta | |
| 6,568,156 B2 | 5/2003 | Silvers et al. | |
| D476,111 S | 6/2003 | Karafotas | |
| D476,884 S | 7/2003 | Miranda | |
| 6,626,313 B2 | 9/2003 | Herbstreit et al. | |
| D480,633 S | 10/2003 | Miranda | |
| D484,585 S | 12/2003 | Upson | |
| D484,646 S | 12/2003 | Ditrichstein | |
| 6,688,795 B1 | 2/2004 | Jacob et al. | |
| D489,148 S | 4/2004 | Sheng | |
| 6,773,187 B2 | 8/2004 | Gueret | |
| D504,979 S | 5/2005 | Lai | |
| D506,850 S | 6/2005 | Angeletta | |
| D507,177 S | 7/2005 | Weissman | |
| D509,890 S | 9/2005 | Stavale | |

(56) References Cited

U.S. PATENT DOCUMENTS

| | | |
|---|---|---|
| D510,991 S | 10/2005 | Harbutt |
| 7,021,849 B2 | 4/2006 | Ramet |
| D522,642 S | 6/2006 | Matsuda |
| D534,076 S | 12/2006 | Green et al. |
| D536,081 S | 1/2007 | Steinel |
| D552,473 S | 10/2007 | Simkin |
| D554,529 S | 11/2007 | Green et al. |
| D561,608 S | 2/2008 | Hogben |
| D562,699 S | 2/2008 | Green et al. |
| D564,900 S | 3/2008 | Green et al. |
| D573,026 S | 7/2008 | Tsai |
| D577,583 S | 9/2008 | Porter et al. |
| D577,584 S | 9/2008 | Porter et al. |
| D578,393 S | 10/2008 | Canamasas Puigbo |
| 7,503,331 B2 | 3/2009 | Eng et al. |
| D592,064 S | 5/2009 | Kilany |
| D592,512 S | 5/2009 | Dubitsky et al. |
| D598,608 S | 8/2009 | Baumer |
| D602,663 S | 10/2009 | Pennington |
| 7,631,781 B2 | 12/2009 | Chen |
| D608,084 S | 1/2010 | Anson et al. |
| D608,650 S | 1/2010 | Eisen |
| D609,103 S | 2/2010 | Marold et al. |
| D609,107 S | 2/2010 | Dubitsky et al. |
| D610,458 S | 2/2010 | Martin |
| D612,245 S | 3/2010 | Canamasas Puigbo |
| D613,616 S | 4/2010 | Renz et al. |
| 7,695,727 B2 | 4/2010 | Magee et al. |
| 7,699,062 B2 | 4/2010 | Sasaki |
| D615,818 S | 5/2010 | Jansen |
| D617,439 S | 6/2010 | Valentino |
| D618,397 S | 6/2010 | Dubitsky et al. |
| D618,398 S | 6/2010 | Dubitsky et al. |
| D625,469 S | 10/2010 | Dubitsky |
| D631,204 S | 1/2011 | Dubitsky et al. |
| 7,878,793 B2 | 2/2011 | Quillin et al. |
| D633,292 S | 3/2011 | Anson et al. |
| D637,806 S | 5/2011 | Anson et al. |
| D644,939 S | 9/2011 | Teller |
| 8,388,252 B2 | 3/2013 | Thiebaut |
| 8,444,337 B2 | 5/2013 | Teller |
| 8,651,308 B1 | 2/2014 | Sung |
| 8,747,002 B2 | 6/2014 | Izkovitz |
| D709,652 S | 7/2014 | Teller |
| D710,544 S | 8/2014 | Shen |
| 8,851,088 B2 | 10/2014 | Dibnah |
| D717,038 S | 11/2014 | Lee |
| 8,888,391 B2 | 11/2014 | Teller et al. |
| D726,028 S | 4/2015 | Thompson |
| D735,413 S | 7/2015 | Smith |
| D737,136 S | 8/2015 | Lam |
| D742,593 S | 11/2015 | Corey |
| 9,232,844 B2 | 1/2016 | Thompson |
| D748,976 S | 2/2016 | Mitchell |
| D758,867 S | 6/2016 | Tsai |
| D762,329 S | 7/2016 | Teller |
| D763,102 S | 8/2016 | Pires |
| 9,585,458 B2 | 3/2017 | Teller et al. |
| 2002/0003983 A1 | 1/2002 | Gueret |
| 2002/0008105 A1 | 1/2002 | Herbstreit et al. |
| 2003/0077102 A1 | 4/2003 | Bourjal |
| 2003/0161851 A1 | 8/2003 | Breha, III et al. |
| 2003/0201201 A1 | 10/2003 | Cheng |
| 2004/0005186 A1 | 1/2004 | Ueda et al. |
| 2006/0076033 A1 | 4/2006 | Bouix |
| 2006/0081721 A1 | 4/2006 | Caserta et al. |
| 2006/0201838 A1 | 9/2006 | Sasaki |
| 2006/0254945 A1 | 11/2006 | Green et al. |
| 2007/0017915 A1 | 1/2007 | Weder et al. |
| 2007/0108092 A1 | 5/2007 | Minuto et al. |
| 2007/0280773 A1 | 12/2007 | Warren |
| 2008/0019758 A1 | 1/2008 | Mallardi |
| 2008/0110854 A1 | 5/2008 | Kelly |
| 2008/0131187 A1 | 6/2008 | Breidenbach et al. |
| 2008/0213028 A1 | 9/2008 | Hosokawa et al. |
| 2009/0022541 A1 | 1/2009 | De LaForcade |
| 2009/0028625 A1 | 1/2009 | Bonneyrat |
| 2011/0024316 A1 | 2/2011 | Ginsburg |
| 2011/0135377 A1 | 6/2011 | Teller |
| 2011/0253731 A1 | 10/2011 | Smith |
| 2013/0302080 A1 | 11/2013 | Teller et al. |
| 2013/0322950 A1 | 12/2013 | Teller |
| 2013/0330427 A1 | 12/2013 | Smigel et al. |
| 2013/0341832 A1 | 12/2013 | Teller et al. |
| 2013/0341833 A1 | 12/2013 | Teller et al. |
| 2014/0013712 A1 | 1/2014 | Teller |
| 2014/0105666 A1 | 4/2014 | Teller |
| 2015/0037082 A1 | 2/2015 | Pires et al. |
| 2015/0096919 A1 | 4/2015 | Thompson |
| 2015/0182004 A1 | 7/2015 | Teller et al. |
| 2016/0262522 A1 | 9/2016 | Teller et al. |
| 2016/0295993 A1 | 10/2016 | Wojcik et al. |
| 2017/0013936 A1 | 1/2017 | Schlatter et al. |

FOREIGN PATENT DOCUMENTS

| | | |
|---|---|---|
| EP | 000031679-0001 | 5/2003 |
| EP | RCD 000031679-0001 | 11/2007 |
| ES | 0505578-01 | 11/2007 |
| FR | 2563711 | 5/1984 |
| FR | 0628393 | 4/1994 |
| FR | 2726443 | 3/1995 |
| FR | 2766339 | 7/1997 |
| FR | 2925263 | 12/2007 |
| GB | 446424 | 10/1935 |
| GB | 2162822 | 5/1985 |
| GB | 2007213 | 5/1990 |
| JP | 1136041 | 3/2002 |
| JP | 455237-001 | 6/2003 |
| JP | 1175238 | 6/2003 |
| JP | 2004106932 | 4/2004 |
| JP | 2001321140 | 11/2004 |
| JP | 2004321410 | 11/2004 |
| JP | 2006-204821 | 9/2006 |
| JP | 3914892 | 2/2007 |
| KR | 20090006972 | 1/2009 |
| WO | WO 2007/007288 | 1/2007 |

OTHER PUBLICATIONS

U.S. Appl. No. 29/411,933, filed Jan. 2012, Teller.
U.S. Appl. No. 13/891,264, filed May 2013, Teller.
U.S. Appl. No. 14/973,717, filed Dec. 2015, Teller.
U.S. Appl. No. 14/988,740, filed Jan. 2016, Teller.
U.S. Appl. No. 15/016,257, filed Feb. 2016, Teller.
U.S. Appl. No. 29/569,183, filed Jun. 2016, Teller.
U.S. Appl. No. 29/569,184, filed Jun. 2016, Teller.
U.S. Appl. No. 29/569,185, filed Jun. 2016, Teller.
U.S. Appl. No. 29/569,186, filed Jun. 2016, Teller et al.
U.S. Appl. No. 29/569,187, filed Jun. 2016, Dubitsky et al.
Born Pretty Store, "1Pc Pro Powder Puff Beauty Cute Egg Shape Sponge Make-up Foundation Makeup (Random Color)", Accessed Nov. 14, 2016. (http://www.bornprettystore.com/powder-puff-beauty-cute-shape-sponge-make-foundation-makeuprandom-color-p-20027.html).
Born Pretty Store, "50Pcs/set Dry Wet Amphibious Sponge Powder Puff Round Rectangle Puff Beauty Makeup Tool", Accessed Nov. 14, 2016. (http://www.bornprettystore.com/50pcsset-amphibious-sponge-powder-puff-round-rectangle-puff-beauty-makeup-tool-p-34825.html).
Claim Chart for CVS products; Jun. 12, 2015.
Claim Chart for Dollar Tree products; Jun. 12, 2015.
Claim Chart for Domestic Industry products; Jun. 12, 2015.
Claim Chart for Five Below products; Jun. 12, 2015.
Claim Chart for Walgreens products; Jun. 12, 2015.
CVS Response to ITC Complaint; Aug. 24, 2015.
Eos Products LLC and The Kind Group LLC Complaint against Oralabs, Inc. et al. In US International Trade Commission; Jun. 12, 2015.

(56) References Cited

OTHER PUBLICATIONS

*Eos Products LLC* v. *Oralabs, Inc. et al.* Complaint in US District Court for the District of Delaware; Jun. 4, 2015.
EP 2509461 Observations by Third Parties; Jan. 16, 2014.
EP 2509461 Observations by Third Parties; Jan. 29, 2016.
EP 2509461 Observations by Third Parties; Jun. 30, 2016.
EP 2509461 Observations by Third Parties; Jun. 9, 2015.
EP 2509461 Observations by Third Parties; Mar. 7, 2016.
EP 2509461 Observations by Third Parties; Oct. 28, 2015.
EP 2509461 Office Action; May 26, 2015.
EP 2509461 Office Action; Oct. 10, 2014.
Five Below Response to ITC Complaint; Aug. 24, 2015.
International Search Report for PCT/US2010/059025 dated Aug. 31, 2011; 2 pages.
Jackson, Junkie Obsession: LancA' me's Baume Baiser, Aug. 13, 2007.
Lancome Baume Baiser (date unclear—for purpous of examination—please consider as prior art).
Letter from John L. Welsh enclosing Draft IPR Petition; Jul. 27, 2015.
Letter from Oralab's Counsel regarding ITC Case; Jul. 20, 2015.
Letter from Oralabs' Counsel regarding ITC Case; Sep. 9, 2015.
Notice of Allowance in U.S. Appl. No. 12/632,114; dated Apr. 18, 2013.
Notice of Allowance in U.S. Appl. No. 13/941,204; dated Nov. 5, 2015.
Notice of Allowance in U.S. Appl. No. 13/941,228; dated Aug. 27, 2014.
Notice of Allowance in U.S. Appl. No. 13/972,896; dated Aug. 1, 2014.
Notice of Allowance in U.S. Appl. No. 13/972,896; dated Nov. 6, 2014.
Notice of Allowance in U.S. Appl. No. 13/972,896; dated Feb. 13, 2015.
Notice of Allowance in U.S. Appl. No. 13/972,896; dated Sep. 18, 2015.
Notice of Allowance in U.S. Appl. No. 13/972,898; dated Aug. 1, 2014.
Notice of Allowance in U.S. Appl. No. 13/972,898; dated Dec. 11, 2014.
Notice of Allowance in U.S. Appl. No. 13/972,898; dated Feb. 2, 2015.
Notice of Allowance in U.S. Appl. No. 13/972,898; dated Jul. 21, 2015.
Notice of Allowance in U.S. Appl. No. 13/972,898; dated Jul. 27, 2015.
Notice of Allowance in U.S. Appl. No. 13/972,898; dated May 14, 2015.
Notice of Allowance in U.S. Appl. No. 13/972,898; dated Oct. 17, 2014.
Notice of Allowance in U.S. Appl. No. 13/972,898; dated Oct. 6, 2015.
Notice of Opposition of EP2509461 and Facts Presented in Support of Opposition, dated May 16, 2017 (21 pages).
Office Action dated Mar. 20, 2015, received in related application No. 201080063211 pending in SIPO.
Office Action in CN201080063211; dated Oct. 8, 2015.
Office Action in CN201510024881.5; dated Apr. 5, 2016.
Office Action in CN201510024881.5; dated Aug. 23, 2016.
Office Action in EP16166294.5-1653; dated Aug. 11, 2016.
Office Action in U.S. Appl. No. 12/632,114; dated Jul. 2, 2012.
Office Action in U.S. Appl. No. 12/632,114; dated Nov. 30, 2012.
Office Action in U.S. Appl. No. 13/891,268; dated Apr. 30, 2015.
Office Action in U.S. Appl. No. 13/941,060; dated Apr. 17, 2015.
Office Action in U.S. Appl. No. 13/941,060; dated Dec. 2, 2013.
Office Action in U.S. Appl. No. 13/941,060; dated Jul. 15, 2014.
Office Action in U.S. Appl. No. 13/941,060; dated Nov. 19, 2014.
Office Action in U.S. Appl. No. 13/941,204; dated Mar. 25, 2015.
Office Action in U.S. Appl. No. 13/941,228; dated Apr. 21, 2014.
Office Action in U.S. Appl. No. 13/941,228; dated Dec. 2, 2013.
Office Action in U.S. Appl. No. 13/972,893; dated Jul. 29, 2015.
Office Action in U.S. Appl. No. 13/972,893; dated Jun. 18, 2014.
Office Action in U.S. Appl. No. 13/972,893; dated Mar. 31, 2015.
Office Action in U.S. Appl. No. 13/972,893; dated Mar. 4, 2014.
Office Action in U.S. Appl. No. 13/972,893; dated Nov. 5, 2013.
Office Action in U.S. Appl. No. 13/972,893; dated Sep. 24, 2014.
Office Action in U.S. Appl. No. 13/972,896; dated Jul. 16, 2015.
Office Action in U.S. Appl. No. 13/972,896; dated Mar. 5, 2014.
Office Action in U.S. Appl. No. 13/972,896; dated May 27, 2015.
Office Action in U.S. Appl. No. 13/972,898; dated Jun. 23, 2015.
Office Action in U.S. Appl. No. 13/972,898; dated Mar. 7, 2014.
Reply to Notice of Opposition of EP2509461, dated Feb. 16, 2018 (14 pages).
Respondents' First Set of Interrogatories to Complainants; dated Aug. 27, 2015.
SIPO Office Action dated Jul. 17, 2014 in connection with CN Appl. No. 201080063211.X JP 2004-321410A and JP 1136041S (listed separately).
Third Party Observations in Application No. EP20100836463; Jun. 15, 2015.
Walgreens' Response to ITC Complaint; Aug. 24, 2015.
Webpage from www.amazon.com showing "Lancome Baume Baiser Hydrating Balm Sensual Massage for Lips" product and images (3 pages).
Webpage http://www.musingsofamuse.com/2009/10/beauty-on-a-budget-eos-lip-b- alm-review.html,Oct. 1, 2009.

LIP BALM WITH SPHERICAL SURFACE AND METHOD FOR PRODUCING

The present application is a continuation of U.S. application Ser. No. 15/441,886, filed Feb. 24, 2017; which is a continuation of U.S. application Ser. No. 15/016,257, filed Feb. 4, 2016 (now U.S. Pat. No. 9,585,458); which is a continuation of U.S. application Ser. No. 13/941,204, filed Jul. 12, 2013 (now abandoned); which is a continuation of U.S. application Ser. No. 13/891,268, filed May 10, 2013 (now abandoned); which is a continuation of U.S. application Ser. No. 12/632,114, filed Dec. 7, 2009 (now U.S. Pat. No. 8,444,337); all of which are incorporated by reference herein.

BACKGROUND OF THE INVENTION

Technical Field

The present invention relates to lip balms and, more particularly, a lip balm having a spherical surface and manufactured using a hot pour process.

Background

Skin on and around the lips can often become chapped or otherwise damaged due to overexposure from elements such as sun and/or wind, particularly during athletic activities in which a person's face remains exposed to these elements for extended periods of time. The same skin can also become chapped or damaged while carrying out everyday non-athletic activities. For example, working outside in extreme cold, dry heat, or sun can also cause damage to the skin on the lips. Even working indoors or sleeping in dry conditions can cause the lips to chap, thereby leading to the development of cracks, which are often painful and can become infected.

Lip balms are often applied to prevent chapped lips. When applied prior to exposure to sun, wind, dry heat, or other extreme conditions, the lip balm can provide suitable protection to the skin on and around the lips. Even when applied after the skin on the lips is chapped, the lip balm can prevent any further damage from occurring. In either case, by providing a protective layer of lip balm, the risk of an infection developing in the damaged skin is minimized.

Lip balms are currently sold as emulsions, liquids, gels, or solids. In emulsion or liquid form, the lip balms are generally packed in containers such as jars. Gels (and liquids on occasion) are typically dispensed from squeeze tubes. Solid lip balms are generally packaged in stick form and dispensable from tubes or from lipstick-type applicators.

Solid lip balms are commonly manufactured using either a hot pour process or a bullet process. In the hot pour process, the lip balm ingredients are combined and heated in a liquefied phase. The liquid is then directly poured into the final consumer package, where it is cooled and solidifies. In the bullet process, the lip balm ingredients are also combined and heated in a liquefied phase. However, in the bullet process, the liquefied balm is poured into molds where it is cooled and solidified. The balm may then be cut into the desired shape and inserted into the consumer package.

The choice of the method used for a particular product depends on the design/functionality of the package, the additives in the balm, and the desired characteristics of the lip balm (color, feel, shape, and the like).

SUMMARY

In one aspect, the present invention resides in a lip balm applicator product that is substantially spherical in shape. The applicator product comprises upper and lower portions that are connectable together to define the substantially spherical shape of the applicator product. A support platform is located in the lower portion and accommodates a quantity of lip balm having an arcuate surface that can be exposed upon separation of the upper portion from the lower portion.

In another aspect, the present invention resides in a lip balm product comprising a composition of waxes and oils in solid form and formed to have an arcuate surface. The wax and oil composition can be eroded upon being drawn across a surface such as a user's lips. The composition is formed to have the arcuate surface using a hot pour process.

In another aspect, the present invention resides in a method of manufacturing a lip balm. In such a method, a receptacle having a concave arcuate surface is provided. A lip balm material in a heated, liquefied phase is also provided and poured into the receptacle. Once poured, the heated, liquefied phase is allowed to solidify such that a surface of the solidified lip balm material has an arcuate configuration that corresponds to the concave arcuate surface of the receptacle.

DETAILED DESCRIPTION

Figure 1:
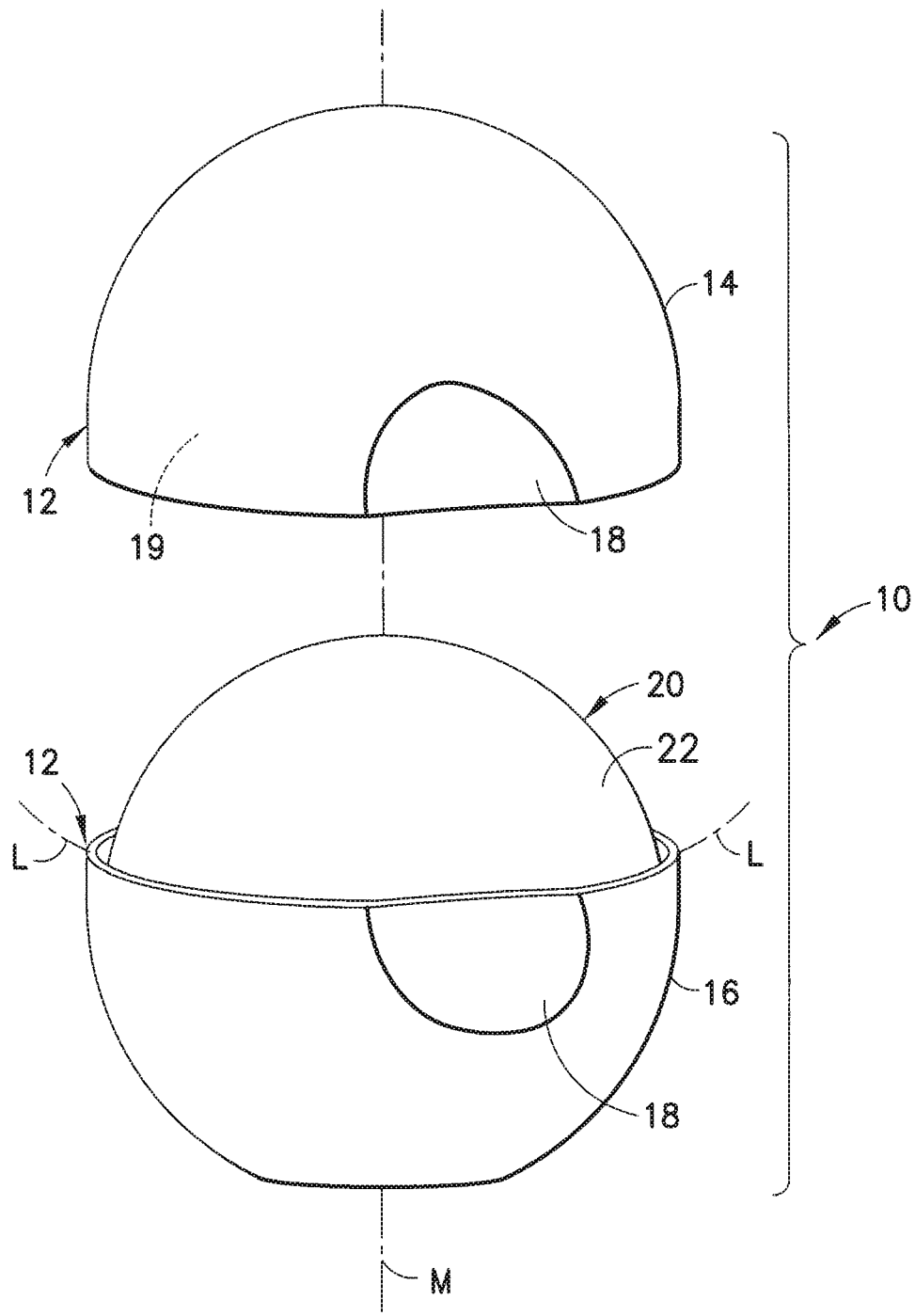
FIG. 1 is a perspective view of a lip balm applicator, of the present invention.

As is shown in FIG. 1, a lip balm applicator product having a lip balm composition is designated generally by the reference number 10 and is hereinafter referred to as "applicator 10." Applicator 10 comprises a receptacle 12 having the lip balm composition located therein. The receptacle 12 is substantially spherical in shape. The present invention is not limited in this regard, as the receptacle 12 may be substantially cylindrical with rounded surfaces, egg-shaped, ovate, or the like. The receptacle 12 comprises an upper portion 14 and a lower portion 16, the portions being separable from each other along a line L that extends substantially circumferentially about the receptacle perpendicular to a major axis M extending longitudinally through the receptacle. An interior surface 19 of the upper portion 14 of the receptacle 12 is defined by a concave surface having a spherical or arcuate topography. Although various surfaces described herein are referred to as being spherical, it should be understood that the term "spherical" includes arcuate surfaces.

The upper portion 14 and the lower portion 16 are connectable together via any suitable means such as the interengagement of threads. The present invention is not limited in this regard, as other mechanisms may be used to connect the upper portion 14 and the lower portion 16 together (e.g., engaging surfaces that fit together frictionally). The lip balm composition is located in the lower portion 16 and is hereinafter referred to as "lip balm 20."

The outer surface of the receptacle 12 includes a depression 18 formed partly on the upper portion 14 and partly on the lower portion 16. The depression 18 is a divot formed in the receptacle 12 that accommodates the thumb of a user to facilitate the opening and closing of the receptacle by alternatingly separating and connecting the upper portion 14 and the lower portion 16.

Upon separation of the upper portion 14 from the lower portion 16, the lip balm 20 is revealed. The lip balm 20 is mounted in the lower portion 16 on a support platform and is defined by a quantity of suitable lip balm material formed or otherwise configured to have a spherical shape that includes a spherical surface 22. The spherical shape and spherical surface 22 allows the lip balm material to extend above the upper edge of the lower portion 16, thereby facilitating the uninhibited application of the lip balm to a user's lips. The present invention is not limited to the lip balm 20 being configured to have a spherical shape and spherical surface 22, however, as other configurations are within the scope of the present invention.

Figure 2:
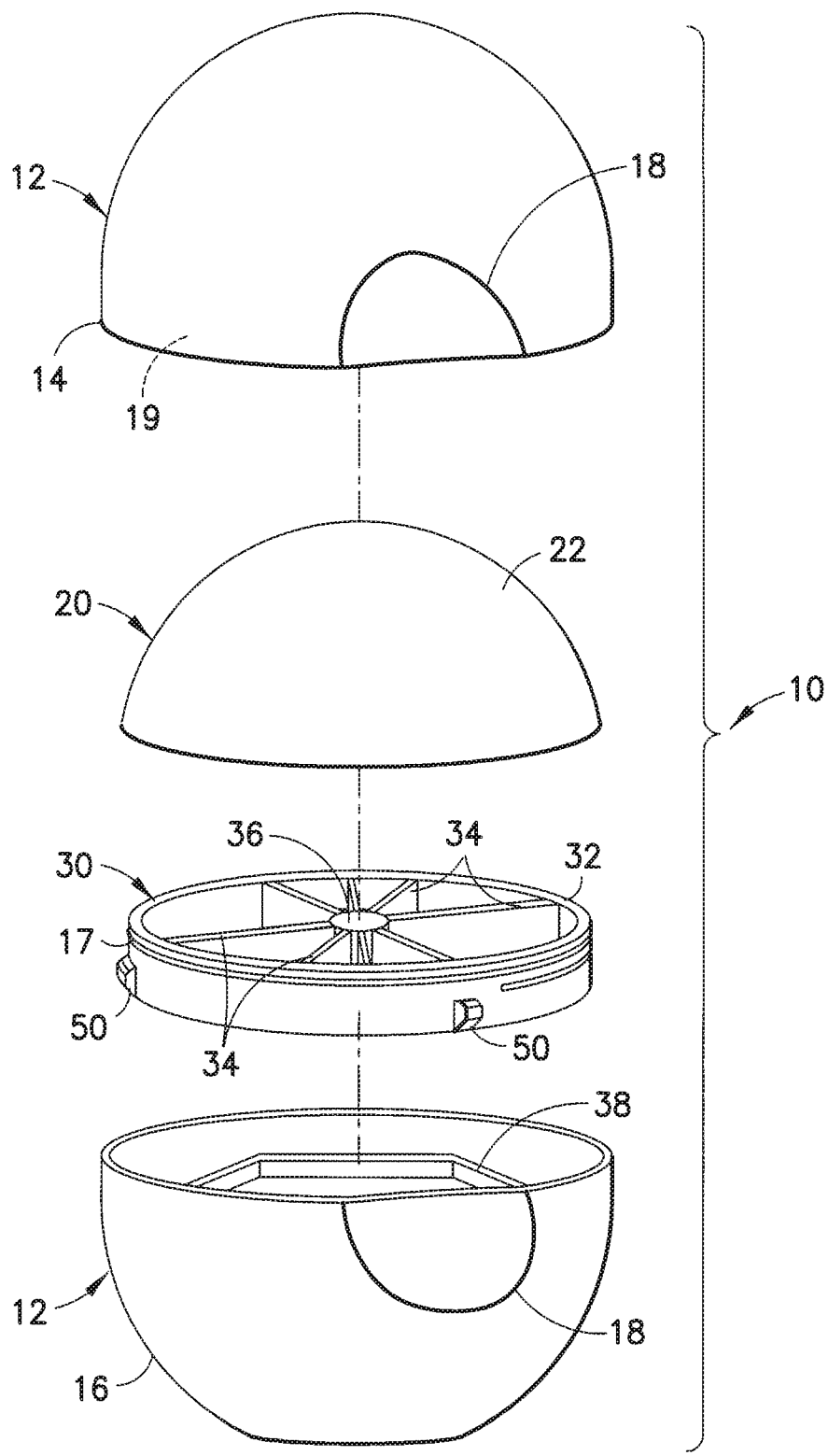
FIG. 2 is a perspective exploded view of the lip balm applicator of FIG. 1.

Referring now to FIG. 2, the support platform on which the lip balm 20 is mounted is designated generally by the reference number 30. The support platform 30 is a wheel having an outer rim 32 and threads 17 located thereon. A plurality of prongs 50 is located along a lower edge of the outer rim 32 (the edge opposite the threads 17) to facilitate the connection of the support platform 30 to connecting structure such as ridges 38 in the lower portion 16. In the assembly of the receptacle 10, the prongs 50 allow the support platform 30 to be snapplingly received on lower portion 16.

The support platform 30 includes a plurality of spokes 34 that extend from the outer rim 32 and that terminate at a hub 36. Both the widths of the spokes 34 and the diameter of the hub 36 are selected to provide a suitable area on which the lip balm 20 can be supported. The spokes 34 extend from the hub 36 at equal angles and connect with an inner surface of the outer rim 32. The present invention is not limited to the use of spokes and hubs, as the area bounded by the outer rim 32 can be solid. Although the outer rim 32 is described as being substantially circular, a portion along the edge of the outer rim is flattened to allow for the accommodation of the depression 18.

Figure 3:
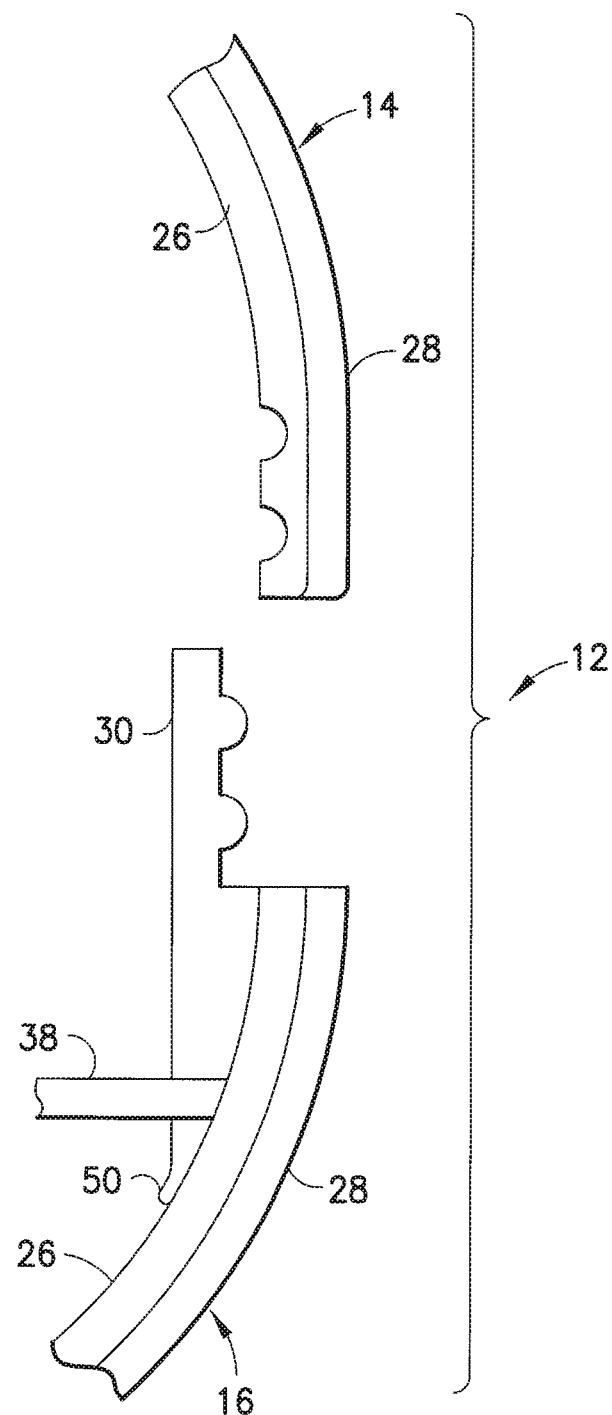
FIG. 3 is a schematic view of a portion of a receptacle of the lip balm applicator of FIG. 1.

Referring now to FIG. 3, both the upper portion 14 and the lower portion 16 of the receptacle 12 comprise a thermoplastic elastomer (TPE) injection molded over a plastic form comprising acrylonitrile-butadiene-styrene (ABS) copolymer. Accordingly, the defining surfaces of both the upper portion 14 and the lower portion 16 comprise a bottom layer 26 of ABS copolymer covered by a top layer 28 of TPE. The present invention is not limited to the bottom layer 26 being ABS copolymer, however, as the bottom layer in one or both of the upper portion 14 and the lower portion 16 can be polyethylene (PE). In such an alternate configuration, the tactile sensation to the user is slightly different upon handling the receptacle 12. In any configuration, the material of the top layer 28 provides a desirable tactile sensation to the user of the applicator 10, namely, by providing a soft surface that can be easily gripped, thereby facilitating the easy opening and closing of the receptacle 12.

The lip balm 20 comprises a quantity of suitable lip balm material. One exemplary lip balm material is a composition that is at least in part a blend of beeswax, coconut oil, olive oil, and jojoba oil that can be eroded when drawn over a surface (e.g., lips). The present invention is not limited to the lip balm material being a blend of such wax and oils, however, as other materials (e.g., petrolatum and petrolatum-based compounds) are within the scope of this disclosure. The blend of beeswax, coconut oil, olive oil, and jojoba oil can also include various ingredients including, but not limited to, emollients, ultraviolet protective agents, moisturizers, vitamins, aloe vera, colorants, fragrances, and the like. Drawing the material over a surface such as the lips causes the material to transfer to the surface as a film.

The spherical outer surface 22 of the lip balm 20 defines a mound-shaped quantity of the lip balm material. The spherical or mound shape provides desirable tactile sensations and use benefits as compared to stick (tubular) forms of the lip balm material. Desirable tactile sensations result from the spherical shape having a larger exposed surface area (as compared to the stick forms of the lip balm material) and the tactile sensation of a curved surface against the lips. Use benefits include the ability to apply the lip balm material to both lips simultaneously.

Figure 4:
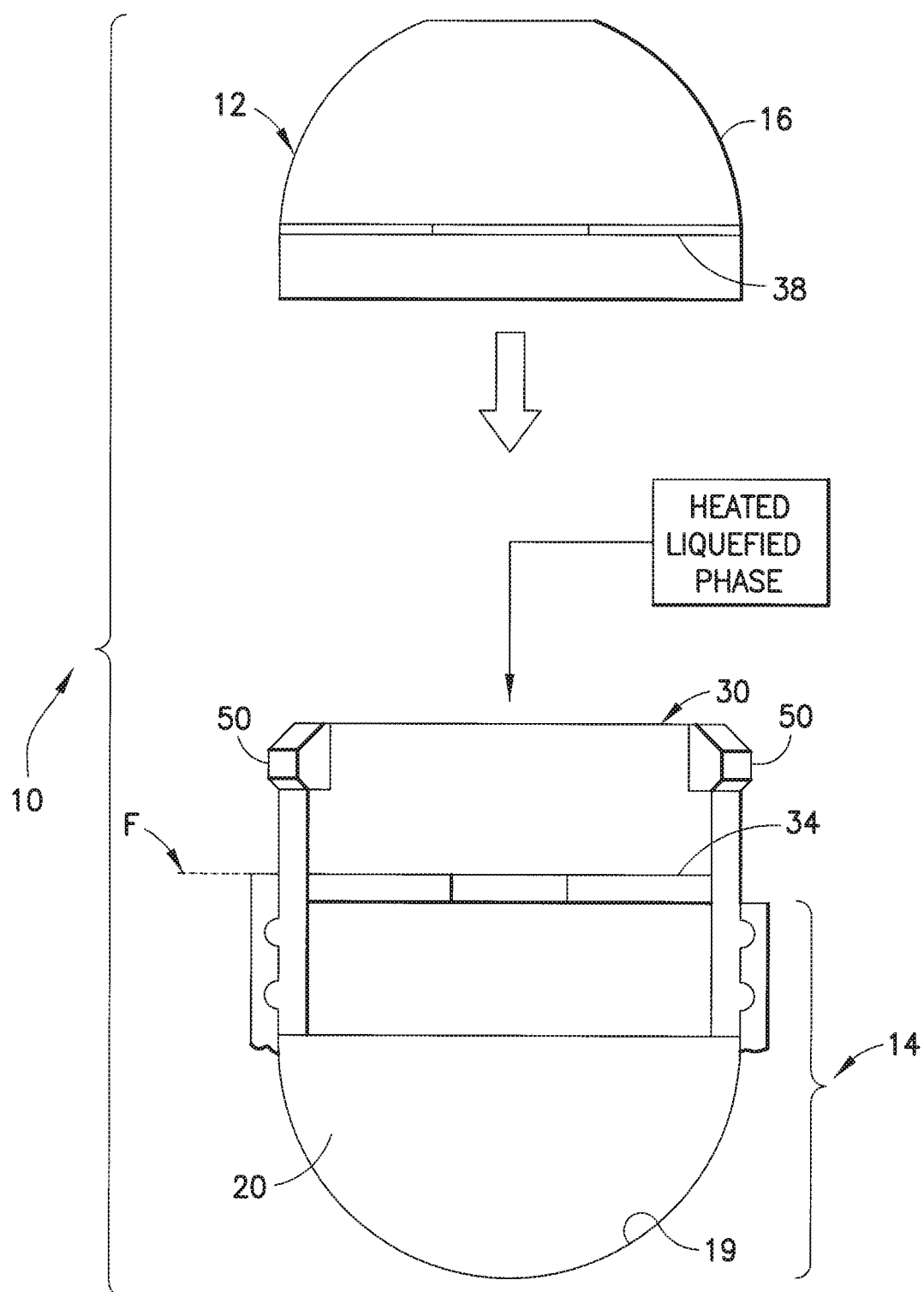
FIG. 4 is a schematic representation of a hot pour process of manufacturing a lip balm having an arcuate surface.

Referring now to FIG. 4, the lip balm 20 is manufactured from the lip balm material using a hot pour process. In using the hot pour process, the lip balm ingredients are combined and heated in a liquefied phase and poured into the final consumer packaging, which in this case is the receptacle 12. In preparation for the hot pour process, the support platform 30 is assembled with the upper portion 14 and inverted such that the support platform is level and vertical with regard to the upper portion. Orienting the assembled upper portion 14 and support platform 30 in this manner allows for the heated and liquefied phase to be poured into the upper portion and retained therein. The interior surface 19 of the upper portion 14 may be coated with a release agent prior to pouring the heated and liquefied phase, which thereby allows for efficient and clean removal of the upper portion by the user when using the finished product.

After the heated and liquefied phase is poured into the upper portion 14 and filled to a level F to cover at least a portion of the spokes 34, the liquefied phase is cooled or allowed to cool. The spokes 34 provide surfaces onto which the solidified lip balm material can adhere. The present invention is not limited to the solidification of the lip balm material around spokes, however, as the support platform can include any suitable configuration of surfaces around which the lip balm material can solidify. Upon sufficient solidification of the lip balm material, the lower portion 16 is inserted onto the assembled and filled upper portion 14 and support platform 30.

The use of the hot pour method in manufacturing the lip balm 20 defined by the spherical surface 22 provides cost benefits over similar methods that use the bullet method. In particular, using the hot pour method obviates the need for an intermediate step in which hot liquid is poured into separate molds, thereby also eliminating the need for additional equipment (molds). Furthermore, the additional steps of removing solidified product from molds and processing and handling the solidified product are avoided.

Although this invention has been shown and described with respect to the detailed embodiments thereof, it will be understood by those of skill in the art that various changes may be made and equivalents may be substituted for elements thereof without departing from the scope of the invention. In addition, modifications may be made to adapt a particular situation or material to the teachings of the invention without departing from the essential scope thereof. Therefore, it is intended that the invention not be limited to the particular embodiments disclosed in the above detailed description, but that the invention will include all embodiments falling within the scope of this disclosure.

We claim:

1. A method of making a lip balm applicator comprising:
   1) assembling an upper portion of the applicator with a support platform;

2) inverting the assembled upper portion and support platform;
3) pouring a liquefied phase of a lip balm material through the support platform into the upper portion such that the liquefied phase of the lip balm material covers at least a portion of the support platform; and
4) coupling a lower portion to the assembled upper portion and support platform;

wherein the upper portion comprises threads located on an interior surface, the support platform comprises threads located on an exterior surface, the upper portion and the lower portion are connectable together via interengagement of the threads located on the interior surface of the upper portion and the threads located on the exterior surface of the support platform, and the support platform comprises an exterior rim and a plurality of support surfaces extending from an interior surface.

2. The method of claim 1, wherein the exterior rim of the support platform is substantially circular.

3. The method of claim 2, further comprising allowing the liquefied phase of the lip balm material to solidify around at least a portion of one of the plurality of support surfaces.

4. The method of claim 3, wherein the upper portion and the support platform are separable from each other along a line that extends substantially circumferentially around the lip balm applicator perpendicular to a major axis of the lip balm applicator, wherein the line of separation is substantially midway between the top and bottom of the lip balm applicator.

5. The method of claim 4, wherein the solidified lip balm material has an application surface that is substantially hemispherical.

6. The method of claim 5, wherein the support platform is substantially wheel-shaped such that a maximum diameter of the support platform is substantially larger than a maximum width of the exterior rim.

7. The method of claim 3, wherein the support platform is connected to the lower portion via prongs.

8. The method of claim 3, wherein the lip balm material comprises petrolatum.

9. The method of claim 8, wherein an outer surface of the lip balm applicator comprises a depression to aid in opening the lip balm applicator.

10. The method of claim 5, wherein an outer surface of the lip balm applicator comprises a gripping surface to aid in opening the lip balm applicator.

11. The method of claim 5, wherein the lower portion is snappingly received by the assembled upper portion and support platform.

12. The method of claim 11, wherein the solidified lip balm material is of the type such that when the solidified lip balm material is mounted on the support platform the solidified lip balm material can resist the torsional forces applied to the mounted solidified lip balm when the upper portion is separated from the lower portion by disengaging the threads located on the interior surface of the upper portion and the threads located on the exterior surface of the support platform.

13. The method of claim 4, wherein the lip balm applicator is symmetrical about the major axis.

14. The method of claim 5, wherein the upper portion is comprised of two layers.

15. The method of claim 12, wherein the upper portion is comprised of two layers.

16. The method of claim 9, wherein the solidified lip balm material has an application surface that is substantially hemispherical.

17. A method of making a lip balm applicator comprising:
1) selecting an assembly comprising an upper portion of the applicator with a support platform;
2) inverting the assembly of the upper portion and the support platform;
3) pouring a liquefied phase of a lip balm material through the support platform into the upper portion such that the liquefied phase of the lip balm material covers at least a portion of the support platform; and
4) completing assembly of the lip balm applicator by connecting a lower portion to the assembly of the upper portion and the support platform;

wherein the support platform comprises an exterior rim and a plurality of support surfaces extending from an interior surface;
wherein the exterior rim of the support platform is substantially circular; and
wherein the upper portion comprises threads located on an interior surface, the support platform comprises threads located on an exterior surface, and the upper portion and the lower portion are connectable together via interengagement of the threads located on the interior surface of the upper portion and the threads located on the exterior surface of the support platform.

18. The method of claim 17, further comprising allowing the liquefied phase of the lip balm material to solidify around at least a portion of one of the plurality of support surfaces.

19. The method of claim 18, wherein the upper portion and the lower portion are separable from each other along a line that extends substantially circumferentially around the lip balm applicator perpendicular to a major axis of the lip balm applicator, wherein the line of separation bisects the major axis at about a midpoint of the major axis.

20. A method of making a lip balm applicator comprising:
1) assembling together an upper portion and a support platform of the applicator such that at least a portion of the support platform is disposed in a cavity formed in the upper portion;
2) manipulating the assembled upper portion and support platform so that the support platform is provided at least adjacent an uppermost portion of the assembly and the cavity formed in the upper portion faces at least in part upwardly;
3) pouring a liquefied phase of a lip balm material through the support platform into the cavity of the upper portion such that the liquefied phase of the lip balm material covers at least a portion of the support platform; and
4) completing assembly of the lip balm applicator by assembling a lower portion to the assembled upper portion and the support platform;

wherein the support platform comprises an exterior rim and a plurality of support surfaces extending from an interior surface;
wherein the upper portion comprises threads located on an interior surface, the support platform comprises threads located on an exterior surface, and the upper portion and the lower portion are connectable together via interengagement of the threads located on the interior surface of the upper portion and the threads located on the exterior surface of the support platform.

21. The method of claim 20, further comprising allowing the liquefied phase of the lip balm material to solidify around at least a portion of one of the plurality of support surfaces.

22. The method of claim 21, wherein the upper portion and the lower portion are separable from each other along a line that extends substantially circumferentially around the lip balm applicator perpendicular to a major axis of the lip balm applicator, wherein the line of separation bisects the major axis at about a midpoint of the major axis.

23. The method of claim 20, wherein the support platform includes a center portion, and the plurality of support surfaces extend between the center portion and the exterior rim.

24. The method of claim 23, wherein the interior surface is formed on one of the center portion and the exterior rim.

25. The method of claim 23, wherein the support platform is substantially wheel-shaped.

26. The method of claim 23, wherein the plurality of support surface radiate outwardly from the center portion.

27. The method of claim 20, wherein the support platform is substantially wheel-shaped such that a maximum diameter of the support platform is substantially larger than both a maximum width and a maximum height of the exterior rim.

28. The method of claim 20, wherein the support platform is connected to the lower portion via prongs.

\* \* \* \* \*